United States Patent
Rao et al.

(10) Patent No.: US 9,505,787 B2
(45) Date of Patent: Nov. 29, 2016

(54) PROCESS FOR PREPARING OF BORTEZOMIB

(71) Applicant: Cipla Limited, Mumbai (IN)

(72) Inventors: Dharmaraj Ramachandra Rao, Thane (IN); Rajendra Narayanrao Kankan, Mumbai (IN); Srinivas Laxminarayan Pathi, Bangalore (IN); Ravikumar Puppala, Bangalore (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 14/427,561

(22) PCT Filed: Sep. 11, 2013

(86) PCT No.: PCT/GB2013/000380
§ 371 (c)(1),
(2) Date: Mar. 11, 2015

(87) PCT Pub. No.: WO2014/041324
PCT Pub. Date: Mar. 20, 2014

(65) Prior Publication Data
US 2015/0246935 A1    Sep. 3, 2015

(30) Foreign Application Priority Data

Sep. 11, 2012   (IN) .................. 2638/MUM/2012

(51) Int. Cl.
*C07D 241/20*     (2006.01)
*C07F 5/02*       (2006.01)
*C07F 5/04*       (2006.01)

(52) U.S. Cl.
CPC ............. *C07F 5/025* (2013.01); *C07D 241/20* (2013.01); *C07F 5/04* (2013.01)

(58) Field of Classification Search
CPC ........ C07D 241/20; C07F 5/025; C07F 5/04; C07F 5/05
USPC .................. 544/229, 406; 558/288
See application file for complete search history.

(56) References Cited

U.S. PATENT DOCUMENTS

| | | | |
|---|---|---|---|
| 5,578,627 A | 11/1996 | Takeda et al. | |
| 5,780,454 A | 7/1998 | Adams et al. | |
| 6,083,903 A * | 7/2000 | Adams .................... | C07F 5/025 514/19.1 |
| 7,714,159 B2 * | 5/2010 | Pickersgill .............. | C07F 5/025 558/288 |

FOREIGN PATENT DOCUMENTS

| | | |
|---|---|---|
| IN | 2638/MUM/2012 | 9/2012 |
| WO | 9613266 A1 | 5/1996 |
| WO | 02059130 A1 | 8/2002 |
| WO | 2005097809 A2 | 10/2005 |
| WO | 2009004350 A1 | 1/2009 |
| WO | 2009036281 A2 | 3/2009 |
| WO | 2010146172 A2 | 12/2010 |
| WO | 2011087822 A1 | 7/2011 |
| WO | 2011098963 A1 | 8/2011 |
| WO | 2012048745 A1 | 4/2012 |
| WO | 2014041324 A1 | 3/2014 |
| WO | 2014041324 A8 | 3/2014 |

OTHER PUBLICATIONS

Foreign communication from the priority application—International Search Report and Written Opinion, PCT/GB2013/000380, Jan. 7, 2014, 19 pages.
Foreign communication from the priority application—International Preliminary Report on Patentability, PCT/GB2013/000380, Mar. 17, 2015, 12 pages.
Dou, Q. Ping, et al., "Bortezomib Millennium Pharmaceuticals," XP002351534, IDrugs, 2002, pp. 828-834, vol. 5, No. 8, PharmaPress Ltd.
Milo, Jr., Lawrence J., et al., "Chemical and Biological Evaluation of Dipeptidyl Boronic Acid Proteasome Inhibitors for Use in Prodrugs and Pro-Soft Drugs Targeting Solid Tumors," XP055058106, Journal of Medicinal Chemistry, 2011, pp. 4365-4377, vol. 54, American Chemical Society.
Tullberg, Marcus, et al., "Efficient synthesis of 2,5-diketopiperazines using microwave assisted heating," XP025002286, Tetrahedron, 2006, pp. 7484-7491, vol. 62, Elsevier Ltd.
Li, Yuexian, et al., "Synthesis of four isotopically labeled forms of a proteasome inhibitor, bortezomib," XP008165112, Journal of Labelled Compounds and Radiopharmaceuticals, 2007, pp. 402-406, vol. 50, John Wiley & Sons, Ltd.

* cited by examiner

*Primary Examiner* — Venkataraman Balasubramanian
(74) *Attorney, Agent, or Firm* — Conley Rose, P.C.; Rodney B. Carroll

(57) ABSTRACT

The present invention provides improved processes for the preparation of Bortezomib, tert -butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenyl-propan-2-yl]carbamate of formula (IV) and N-{(1S)-3-methyl-1-[(3aS,4S,6S,7aS)-3a,5,5-trimethylhexahydro-4,6-methano-1,3,2-benzodioxaborol-2-yl]butyl} phenylalanine of formula (V). Compound (IV) is prepared by coupling (1R)-3-methyl-1-[(3aS,4S,6S,7aR)-3a,5,5-trimethyl-hexahydro-4,6-methano-1,3,2-benzodioxaborol-2-yl]butan-1-amine of formula (II) or its salt with N-(tert-butoxycarbonyl)-L -phenylalanine of formula (III) in a first solvent in the presence of a first coupling agent and a first base, wherein the coupling process does not comprise solvent exchange. Compound (V) is prepared by deprotecting compound (IV) using an alcoholic solution of an inorganic acid.

24 Claims, No Drawings

PROCESS FOR PREPARING OF BORTEZOMIB

CROSS REFERENCE TO RELATED APPLICATIONS

This application is a filing under 35 U.S.C. 371 of International Application No. PCT/GB2013/000380 filed Sep. 11, 2013, entitled "Process for Preparing of Bortezomib," which claims priority to Indian Patent Application No. 2638/MUM/2012 filed Sep. 11, 2012, which applications are incorporated by reference herein in their entirety.

TECHNICAL FIELD OF THE INVENTION

The present invention relates to improved processes for the preparation of Bortezomib and intermediates of Bortezomib.

BACKGROUND OF THE INVENTION

Bortezomib is a modified dipeptidyl boronic acid derivative derived from leucine and phenyl alanine. The chemical name is [(1R)-3-methyl-1-[[(2S)-1-oxo-3-phenyl-2-[(pyrazinylcarbonyl)amino]propyl]amino]butyl] boronic acid and represented as follows:

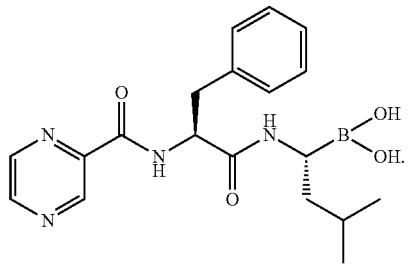

(I)

U.S. Pat. No. 5,780,454 discloses Bortezomib while WO02059130 describes the mannitol ester of Bortezomib.

In U.S. Pat. No. 5,780,454, the preparation of Bortezomib is not exemplified. WO2005097809 describes large scale preparation of Bortezomib wherein the reaction is carried out in the presence of 2-(1H-benzotriazol-1-yl)-1,1,3,3-tetramethyluronium tetrafluoroborate (TBTU), tertiary amine and in dichloromethane as a solvent and which involves solvent exchange to replace dichloromethane with ethyl acetate.

There are other patent applications such as WO2009004350, WO2009036281, WO2010146172, WO2011087822, WO2011098963 and WO2012048745 which describe various processes for the synthesis of Bortezomib.

WO2009004350 and WO2009036281 describe the condensation of N-(pyrazinylcarbonyl)-L-phenylalanine with 4,6-methano-1,3,2-benzodioxaborole-2-methanamine, hexahydro-3a,5,5-trimethyl-α-(2-methylpropyl)-(αR,3aS,4S,6S,7aR)-trifluoro acetate.

WO2010146172 describes the preparation of 4,6-methano-1,3,2-benzodioxaborole-2-methanamine, hexahydro-3a,5,5-trimethyl-α-(2-methylpropyl)-(αR,3aS,4S,6S,7aR)-trifluoro acetate.

WO2011087822 describes the preparation of Bortezomib by deprotection of (2S)-N-[(1R)-1-(1,3,6,2-dioxazaborocan-2-yl)-3-methylbutyl-3-phenyl-2-(pyrazin-2-yl formamido)propanamide.

WO2011098963 describes the preparation of Bortezomib wherein any 2 steps of last 3 steps are carried out without isolation of the intermediates.

WO2012048745 describes the preparation of Bortezomib using cyclic phosphonic acid anhydride as a coupling agent.

The prior art processes require the use of halogenated solvents, solvent exchange and tedious work up procedures and hence, result in a poor yield.

Thus, there is a need to develop an industrially feasible, economic process and which provides the product with improved yield, and improved chemical purity as well as optical purity.

SUMMARY OF THE INVENTION

According to a first aspect of the present invention, there is provided an improved process for the preparation of Bortezomib.

The process comprises:
a) coupling (1R)-3-methyl-1-[(3aS,4S,6S,7aR)-3a,5,5-trimethylhexahydro-4,6-methano-1,3,2-benzodioxaborol-2-yl]butan-1-amine of formula (II) or its salt

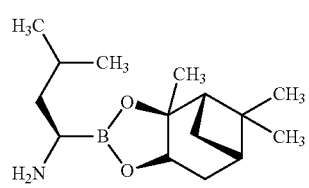

(II)

with N-(tert-butoxycarbonyl)-L-phenylalanine of formula (III)

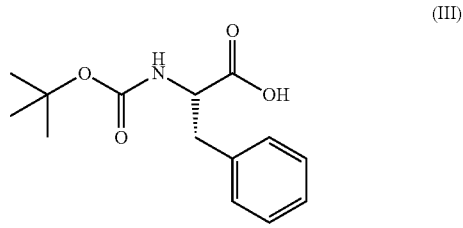

(III)

in a first solvent in the presence of a first coupling agent and a first base to obtain tert-butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenylpropan-2-yl]carbamate of formula (IV);

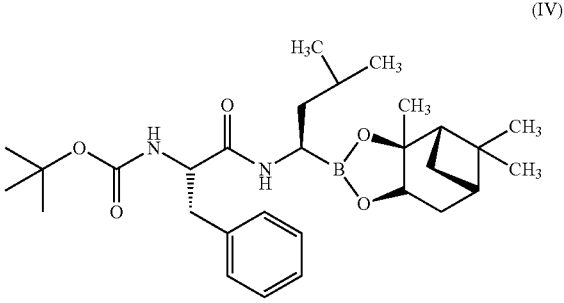

(IV)

b) deprotecting tert-butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenylpropan-2-yl]carbamate of formula (IV) using an alcoholic solution of an inorganic acid to obtain N-{(1S)-3-methyl-1-[(3aS,4S,6S,7aS)-3a,5,5-trimethylhexahydro-4,6-methano-1,3,2-benzodioxaborol-2-yl]butyl} phenylalanine of formula (V) or its salt;

(V)

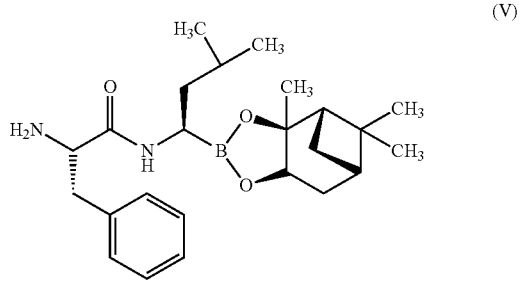

c) coupling compound (V) or its salt with pyrazine-2-carboxylic acid of formula (VI)

(VI)

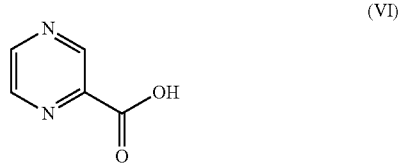

in a second solvent in the presence of a second coupling agent and a second base to obtain N -{(1R)-3-methyl-1-[(3aS,4S,6S,7aS)-3a,5,5-trimethylhexahydro-4,6-methano-1,3,2-benzodioxaborol-2-yl]butyl}-Nα-(pyrazin-2-ylcarbonyl)-L-phenylalaninamide of formula (VII).

(VII)

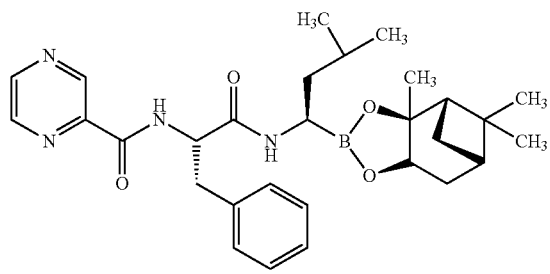

d) deprotecting compound (VII) to obtain Bortezomib or its anhydride.

According to a second aspect of the present invention, there is provided a process comprising a) coupling (1R)-3-methyl-1-[(3aS,4S,6S,7aR)-3a,5,5-trimethylhexahydro-4,6-methano-1,3,2-benzodioxaborol-2-yl]butan-1-amine of formula (II) or its salt with N-(tert -butoxycarbonyl)-L-phenylalanine of formula (III) in a first solvent in the presence of a first coupling agent and a first base to obtain tert-butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenylpropan-2-yl]carbamate of formula (IV) wherein the process does not comprise solvent exchange.

According to a third aspect of the present invention, there is provided a process comprising b) preparing N-{(1S)-3-methyl-1-[(3aS,4S,6S,7aS)-3a,5,5-trimethylhexa-hydro-4,6-methano-1,3,2-benzodioxaborol-2-yl]butyl} phenylalanine of formula (V) or its salt by deprotecting tert-butyl[1-({(1S)-3-methyl-1-[(3aS,4S,6S,7aS)-3a,5,5-trimethylhexa-hydro-4,6-methano-1,3,2-benzodioxaborol-2-yl] butyl}amino)-1-oxo-3-henylpropan-2-yl]carbamate of formula (IV) using an alcoholic solution of an inorganic acid.

DETAILED DESCRIPTION OF THE INVENTION

The present invention relates to processes for the preparation of Bortezomib or intermediates of Bortezomib, which processes help to reduce the formation of impurities such as deboronated impurity (VIII) and dimer impurity (IX).

(VIII)

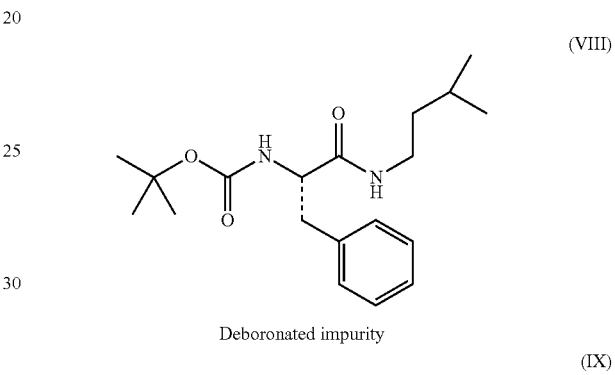

Deboronated impurity (IX)

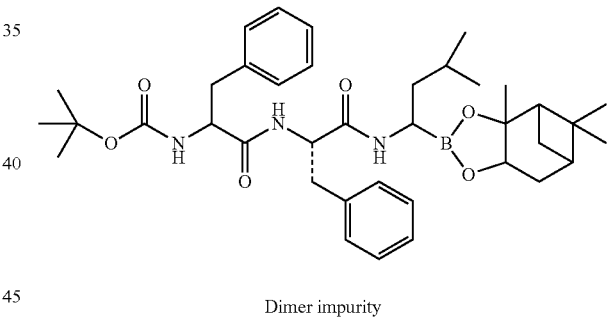

Dimer impurity

The improved process for preparing Bortezomib comprises
a) coupling compound (II) or its salt with compound (III) in a first solvent in the presence of a first coupling agent and a first base to obtain compound (IV);
b) deprotecting compound (IV) using an alcoholic solution of an inorganic acid to obtain compound (V) or its salt;
c) coupling compound (V) or its salt with compound (VI) in a second solvent in the presence of a second coupling agent and a second base to compound (VII); and
d) deprotecting compound (VII) to obtain Bortezomib or its anhydride.

The improved process for preparing compound (IV) comprises a) coupling compound (II) or its salt with compound (III) in a first solvent in the presence of a first coupling agent and a first base wherein the process does not comprise solvent exchange. This process may be combined with step b), with steps b) and c), or with steps b), c) and d).

The inventors have found that avoiding solvent exchange in step a) avoids the degradation of compound (IV) and so helps to reduce the formation of impurities such as deboronated impurity (VIII) and dimer impurity (IX). Also as an additional solvent is not necessary, the cost and the time cycle of step a) is reduced. Therefore, the coupling of compound (II) or its salt with compound (III) is preferably carried out without exchanging the first solvent for another solvent, i.e. the coupling process may not comprise solvent exchange. This feature applies to both the first and second aspect of the present invention.

The first solvent may be selected from the group consisting of dichloromethane, dichloroethane, toluene, dimethyl formamide, dimethyl sulfoxide and mixtures thereof. Preferably the first solvent is dichloromethane.

The first coupling agent may be selected from the group consisting of O-(benzotriazol-1-yl)-N,N,N',N'-tetramethyluronium tetrafluoroborate (TBTU), dicyclohexylcarbodiimide (DCC), O-benzotriazole-N,N',N'-tetramethyl uronium hexafluoro phosphate (HBTU), benzotriazol-1-yloxytripyrrolidinophosphonium hexafluorophosphate and 1-ethyl-3-(3-dimethylaminopropyl)carbodiimide hydrochloride (EDC HCl).

An additive may be used to inhibit side reactions and reduce racemization. Therefore, the first coupling agent may be used with a first additive. The first additive may be selected from the group consisting of 1-hydroxybenzotriazole (HOBT), N-hydroxysuccinimide (HOSu), 2-hydroxypyridine-N-oxide (HOPO), 1-hydroxy-7-azabenzotriazole (HOAt) and N-hydroxy-5-norbornene-2,3-dicarboximide (HONB).

Preferably the first coupling agent is EDC HCl and the first additive is HOBt.

The first base may be selected from the group consisting of N,N-diisopropyl ethyl amine and triethyl amine.

These features apply to both the first and second aspects of the present invention.

The improved process for deprotecting compound (IV) comprises b) deprotecting compound (IV) using an alcoholic solution of an inorganic acid to obtain compound (V) or its salt. This process may be combined with step a), with steps a) and c), with steps a), c) and d), with step c) or with steps c) and d).

The inventors have found that using an alcoholic solution of an inorganic acid during the deprotection of compound (IV) also helps to control the formation of impurities.

The inorganic acid used may be selected from the group consisting of hydrochloric acid, hydrobromic acid and sulphuric acid.

The alcohol used may be selected from the group consisting of ethanol, methanol, isopropanol and mixtures thereof.

Preferably the alcoholic solution of an inorganic acid is isopropanolic hydrochloric acid.

The deprotection of compound (IV) may be carried out at a temperature of from 15 to 35° C., preferably from 20 to 30° C.

The deprotection of compound (IV) may be carried out in situ without isolation of the compound of formula (IV).

These features apply to both the first and third aspects of the present invention.

As described above, the process for the preparation of Bortezomib and the process for preparing compound (IV) avoid the solvent exchange step required by WO2005097809. Also it is observed that impurities such as deboronated impurity (VIII) and dimer impurity (IX) are found to be below the detectable limit compared to the impurities present in a sample of compound (IV) obtained by following the process described in WO2005097809. Also the product obtained is of higher purity. As described above, use of an alcoholic solution of an inorganic acid in step b) also helps to control the formation of impurities. Since the impurities are controlled during step a) and step b), the Bortezomib subsequently obtained by the claimed process for the preparation of Bortezomib is of higher purity and comprises deboronated impurity (VIII) and dimer impurity (IX) below the detectable limit.

| Impurity data* | Compound of formula (IV) obtained by the process of the present invention | Compound of formula (IV) obtained by following process described in WO2005097809 |
| --- | --- | --- |
| Deboronated impurity | Not detected | 8.75% |
| Dimer impurity | Not detected | 0.57% |
| Chromatographic purity of Compound of formula (IV) | 95.53% | 83.88% |

*impurity data obtained by HPLC on a Dionex Ultimate 3000 using sodium dihydrogen phosphate (Sigma Aldrich/Merck) and acetonitrile (standard reagent, HPLC grade)

The coupling of compound (V) or its salt with pyrazine-2-carboxylic acid of formula (VI) is carried out in a second solvent in the presence of a second coupling agent and a second base to obtain N-{(1R)-3-methyl-1-[(3aS,4S,6S,7aS)-3a,5,5-trimethylhexahydro-4,6-methano-1,3,2-benzodioxaborol-2-yl]butyl}-Nα-(pyrazin-2-ylcarbonyl)-L-phenyl alaninamide of formula (VII).

The second solvent may be selected from the group consisting of toluene and ethyl acetate. Preferably the second solvent is toluene.

The second coupling agent and second base may be selected from the list of coupling agents suitable for use as the first coupling agent and the list of bases suitable for use as the first base given above. Preferably the second coupling agent is TBTU.

The second coupling agent may be used with a second additive. The second additive may be selected from the list of additives suitable for use as the first additive given above.

The deprotection of the compound of formula (VII) to obtain Bortezomib or its anhydride may be carried out by treating the compound of formula (VII) with a boronic acid acceptor in an alcoholic solvent.

The boronic acid acceptor may be selected from the group consisting of isobutyl boronic acid, 2-methyl-1-propyl boronic acid, trifluoroacetic acid, hydrochloric acid, hydrobromic acid and mixtures thereof.

The alcoholic solvent may be selected from group consisting of ethanol, methanol, isopropanol, n-propanol, n-butanol, isobutanol and mixtures thereof.

In an embodiment, the process for the preparation of Bortezomib of the present invention can be represented as shown in the following reaction scheme:

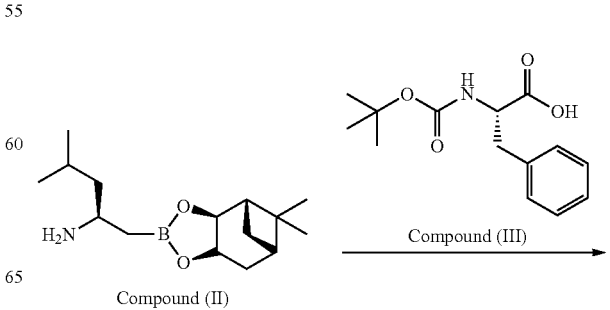

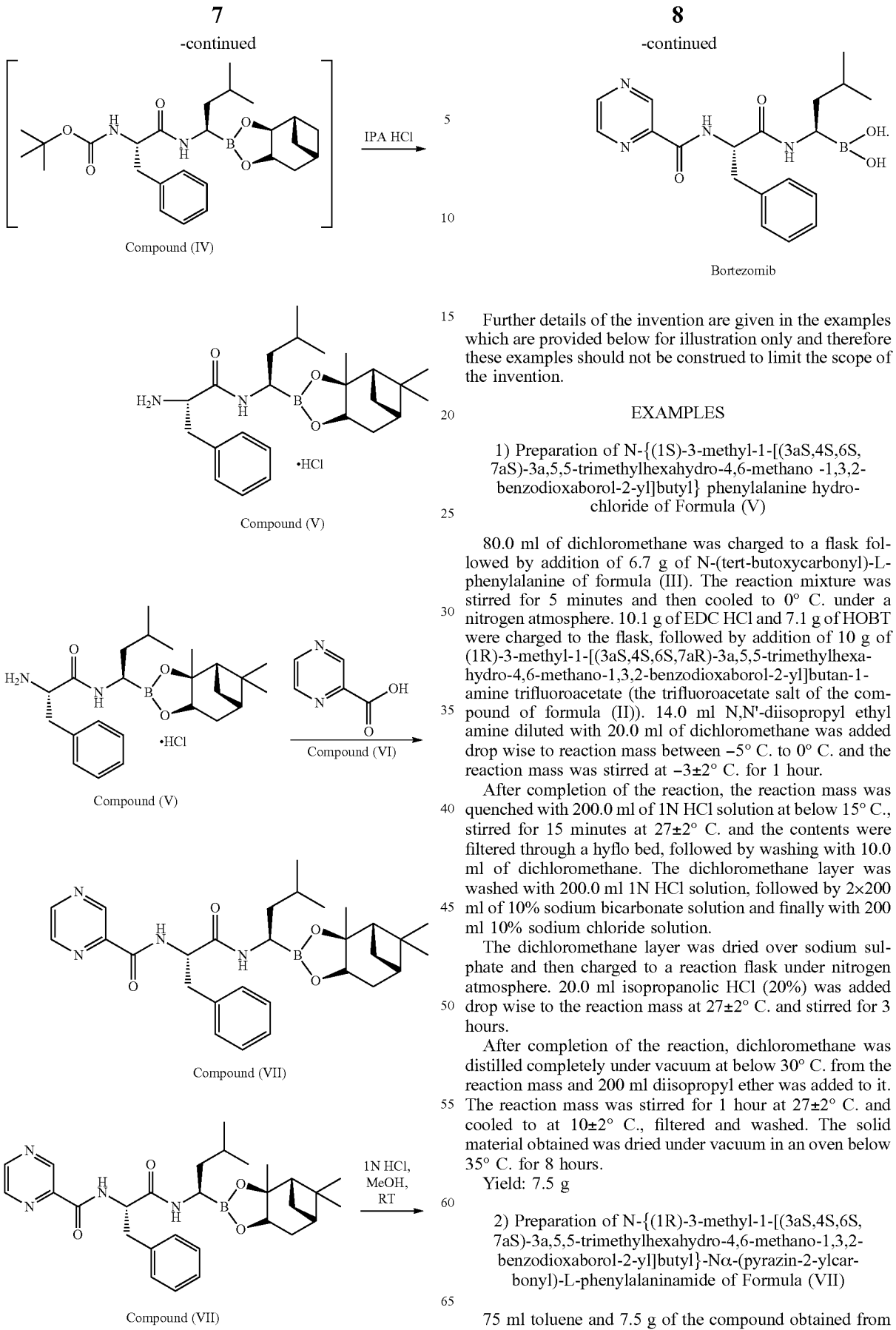

Further details of the invention are given in the examples which are provided below for illustration only and therefore these examples should not be construed to limit the scope of the invention.

EXAMPLES

1) Preparation of N-{(1S)-3-methyl-1-[(3aS,4S,6S,7aS)-3a,5,5-trimethylhexahydro-4,6-methano -1,3,2-benzodioxaborol-2-yl]butyl} phenylalanine hydrochloride of Formula (V)

80.0 ml of dichloromethane was charged to a flask followed by addition of 6.7 g of N-(tert-butoxycarbonyl)-L-phenylalanine of formula (III). The reaction mixture was stirred for 5 minutes and then cooled to 0° C. under a nitrogen atmosphere. 10.1 g of EDC HCl and 7.1 g of HOBT were charged to the flask, followed by addition of 10 g of (1R)-3-methyl-1-[(3aS,4S,6S,7aR)-3a,5,5-trimethylhexahydro-4,6-methano-1,3,2-benzodioxaborol-2-yl]butan-1-amine trifluoroacetate (the trifluoroacetate salt of the compound of formula (II)). 14.0 ml N,N'-diisopropyl ethyl amine diluted with 20.0 ml of dichloromethane was added drop wise to reaction mass between −5° C. to 0° C. and the reaction mass was stirred at −3±2° C. for 1 hour.

After completion of the reaction, the reaction mass was quenched with 200.0 ml of 1N HCl solution at below 15° C., stirred for 15 minutes at 27±2° C. and the contents were filtered through a hyflo bed, followed by washing with 10.0 ml of dichloromethane. The dichloromethane layer was washed with 200.0 ml 1N HCl solution, followed by 2×200 ml of 10% sodium bicarbonate solution and finally with 200 ml 10% sodium chloride solution.

The dichloromethane layer was dried over sodium sulphate and then charged to a reaction flask under nitrogen atmosphere. 20.0 ml isopropanolic HCl (20%) was added drop wise to the reaction mass at 27±2° C. and stirred for 3 hours.

After completion of the reaction, dichloromethane was distilled completely under vacuum at below 30° C. from the reaction mass and 200 ml diisopropyl ether was added to it. The reaction mass was stirred for 1 hour at 27±2° C. and cooled to at 10±2° C., filtered and washed. The solid material obtained was dried under vacuum in an oven below 35° C. for 8 hours.

Yield: 7.5 g

2) Preparation of N-{(1R)-3-methyl-1-[(3aS,4S,6S,7aS)-3a,5,5-trimethylhexahydro-4,6-methano-1,3,2-benzodioxaborol-2-yl]butyl}-Nα-(pyrazin-2-ylcarbonyl)-L-phenylalaninamide of Formula (VII)

75 ml toluene and 7.5 g of the compound obtained from example 1 were charged into a reaction flask under nitrogen atmosphere followed by addition of 2.33 g of pyrazine-2-carboxylic acid of formula (VI) and 6.0 g of TBTU. The reaction mixture was stirred for 10 minutes and cooled to 0±5° C. 12 ml N,N'-diisopropyl ethyl amine diluted with 15.0 ml of toluene was added drop wise to the reaction mass and the reaction mass was warmed to 25° C. and stirred for 3 hours.

After completion of the reaction, the reaction mass was washed with 2×75 ml purified water. The layers were separated and the toluene layer was washed with 75 ml of 1% phosphoric acid solution, 75 ml of 2% potassium carbonate solution and finally with 75 ml of 10% sodium chloride solution. The toluene layer was dried with sodium sulphate and distilled completely under vacuum at below 35° C.

Yield: 8.0 g

3) Preparation of Bortezomib 8 g of the compound obtained from example 2 was dissolved in 64.0 ml of methanol in a reaction flask. 64.0 ml of heptane was added to the solution at room temperature followed by addition of 2.5 g of 2-methyl-1-propyl boronic acid. 42.0 ml of 1N hydrochloric acid solution was added drop wise and the reaction mass was stirred for 12 hours.

After completion of the reaction, the heptane layer was separated and discarded. The aqueous methanol layer was washed with more heptane and then concentrated at 35° C. under vacuum to remove the methanol completely. The residue obtained was dissolved in 57.0 ml of dichloromethane and cooled to 3±2° C. The pH of the solution was adjusted to 12±0.1 with 2N NaOH solution. The dichloromethane layer was separated and the aqueous layer was washed with more dichloromethane. The aqueous layer was transferred to a clean flask and cooled to 3±2° C. 80 ml of 2N HCl was then added and the reaction mass was extracted with dichloromethane. The dichloromethane was washed with saturated brine solution till the pH of the washings was neutral. The dichloromethane layer was dried over sodium sulphate and dichloromethane was evaporated below 35° C. under vacuum. To the oil obtained, 34.0 ml of acetone was added and distilled at below 50° C. followed by further addition of 63.0 ml of fresh acetone and the reaction mass was stirred at 25° C., cooled to 5±2° C. and stirred. The solid obtained was filtered, washed with chilled acetone and then dried in vacuum at 43±2° C. for 10 hours.

Yield: 4.0 g
Purity: 99.6%
Chiral purity—More than 99.8%

4) Preparation of N-{(1S)-3-methyl-1-[(3aS,4S,6S,7aS)-3a,5,5-trimethylhexahydro-4,6-methano-1,3,2-benzodioxaborol-2-yl]butyl} phenylalanine hydrochloride of Formula (V)

400.0 ml of dichloromethane was charged to a flask followed by addition of 33.5 g of N-(tert-butoxycarbonyl)-L-phenylalanine of formula (III). The reaction mixture was stirred for 5 minutes and then cooled to 0° C. under a nitrogen atmosphere. 50.5g of EDC HCl and 35.5 g of HOBT were charged to the flask, followed by addition of 50 g of (1R)-3-methyl-1-[(3aS,4S,6S,7aR)-3a,5,5-trimethyl-hexahydro-4,6-methano-1,3,2-benzodioxaborol-2-yl]butan-1-amine trifluoroacetate (the trifluoroacetate salt of the compound of formula (II)). 70.0 ml N,N'-diisopropyl ethyl amine diluted with 100.0 ml of dichloromethane was added drop wise to reaction mass between −5° C. to 0° C. and the reaction mass was stirred at −3±2° C. for 1 hour.

After completion of the reaction, the reaction mass was quenched with 1000.0 ml of 1N HCl solution at below 15° C., stirred for 15 minutes at 27±2° C. and the contents were filtered through a hyflo bed, followed by washing with 50.0 ml of dichloromethane. The dichloromethane layer was washed with 1000.0 ml 1N HCl solution, followed by 2×1000 ml of 10% sodium bicarbonate solution and finally with 1000 ml 10% sodium chloride solution.

The dichloromethane layer was dried over sodium sulphate and then charged to a reaction flask under nitrogen atmosphere. 100.0 ml isopropanolic HCl (20%) was added drop wise to the reaction mass at 27±2° C. and stirred for 3 hours.

After completion of the reaction, dichloromethane was distilled completely under vacuum at below 30° C. from the reaction mass and 1000 ml diisopropyl ether was added to it. The reaction mass was stirred for 1 hour at 2±2° C. and cooled to at 10±2° C., filtered and washed. The solid material obtained was dried under vacuum in an oven below 35° C. for 8 hours.

Yield: 40.0 g

5) Preparation of N-{(1R)-3-methyl-1-[(3aS,4S,6S,7aS)-3a,5,5-trimethylhexahydro-4,6-methano-1,3,2-benzodioxaborol-2-yl]butyl}-Nα-(pyrazin-2-ylcarbonyl)-L-phenylalaninamide of Formula (VII)

400 ml toluene and 40.0 g of the compound obtained from example 4 were charged into a reaction flask under nitrogen atmosphere followed by addition of 12.2 g of pyrazine-2-carboxylic acid of formula (VI) and 32.0 g of TBTU. The reaction mixture was stirred for 10 minutes and cooled to 0±5° C. 64.0 ml N,N'-diisopropyl ethyl amine diluted with 80.0 ml of toluene was added drop wise to the reaction mass and the reaction mass was warmed to 25° C. and stirred for 3 hours.

After completion of the reaction, the reaction mass was washed with 2×400 ml purified water. The layers were separated and the toluene layer was washed with 400 ml of 1% phosphoric acid solution, 400 ml of 2% potassium carbonate solution and finally with 400 ml of 10% sodium chloride solution. The toluene layer was dried with sodium sulphate and distilled completely under vacuum at below 37° C.

Yield: 46.0 g

6) Preparation of Bortezomib 46 g of the compound obtained from example 5 was dissolved in 368.0 ml of methanol in a reaction flask. 368.0 ml of heptane was added to the solution at room temperature followed by addition of 14.72 g of 2-methyl-l-propyl boronic acid. 230.0 ml of 1N hydrochloric acid solution was added drop wise and the reaction mass was stirred for 12 hours.

After completion of the reaction, the heptane layer was separated and discarded. The aqueous methanol layer was washed with more heptane and then concentrated at 35° C. under vacuum to remove the methanol completely. The residue obtained was dissolved in 368.0 ml of dichloromethane and cooled to 3±2° C. The pH of the solution was adjusted to 12±0.1 with 2N NaOH solution. The dichloromethane layer was separated and the aqueous layer was washed with more dichloromethane. The aqueous layer was transferred to a clean flask and cooled to 3±2° C. 460.0 ml of 2N HCl was then added and the reaction mass was extracted with dichloromethane. The dichloromethane was washed with saturated brine solution till the pH of the washings was neutral. The dichloromethane layer was dried over sodium sulphate and dichloromethane was evaporated below 35° C. under vacuum. To the oil obtained, 184.0 ml of acetone was added and distilled at below 50° C. followed by further addition of 368.0 ml of fresh acetone and the reaction mass was stirred at 25° C., cooled to 5±2° C. and stirred. The solid obtained was filtered, washed with chilled acetone and then dried in vacuum at 43±2° C. for 10 hours.

Yield: 22.0 g
Purity: 99.7%
Chiral purity—99.87%

The invention claimed is:

1. A process for the preparation of Bortezomib, said process comprising:
   a) coupling (1R)-3-methyl-1-[(3aS,4S,6S,7aR)-3a5,5-trimethylhexahydro-4,6-methano-1,3,2-benzodioxaborol-2-yl]butan-1-amine of formula (II) or its salt

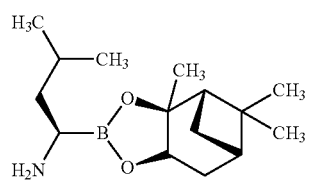

with N-(tert-butoxycarbonyl)-L-phenylalanine of formula (III)

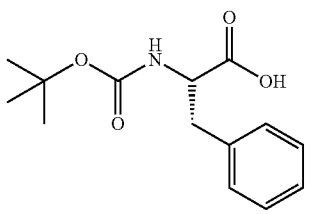

in a first solvent in the presence of a first coupling agent and a first base to obtain tert-butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenylpropan-2-yl]carbamate of formula (IV) wherein step a) does not comprise solvent exchange;

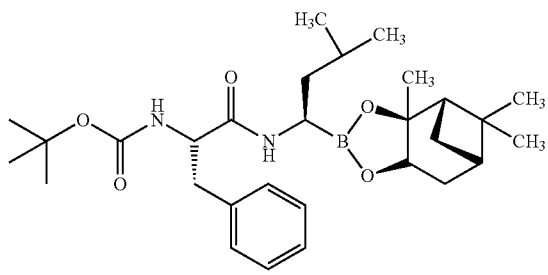

b) deprotecting tert-butyl[1-({(1S)-3-methyl-1-[(3aS,4S,6S,7aS)-3a,5,5-trimethylhexahydro-4,6-methano-1,3,2-benzodioxaborol-2-yl]butyl}amino)-1-oxo-3-phenylpropan-2-yl]carbamate of formula (IV) using an alcoholic solution of an inorganic acid to obtain N-{(1S)-3-methyl-1-[(3aS,4S,6S,7aS)-3a,5,5-trimethylhexahydro-4,6-methano-1,3,2-benzodioxaborol-2-yl]butyl}phenylalanine of formula (V) or its salt;

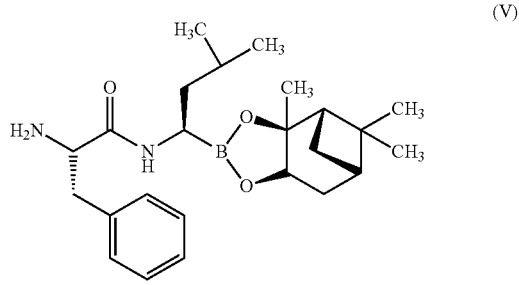

c) coupling the compound of formula (V) or its salt with pyrazine-2-carboxylic acid of formula (VI)

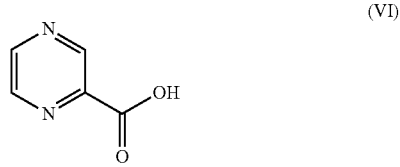

in a second solvent in the presence of a second coupling agent and a second base to obtain N-{(1R)-3-methyl-1-[(3aS,4S,6S,7aS)-3a,5,5-trimethylhexahydro-4,6-methano-1,3,2-benzodioxaborol-2-yl]butyl}-Nα-(pyrazin-2-ylcarbonyl)-L-phenylalaninamide of formula (VII); and

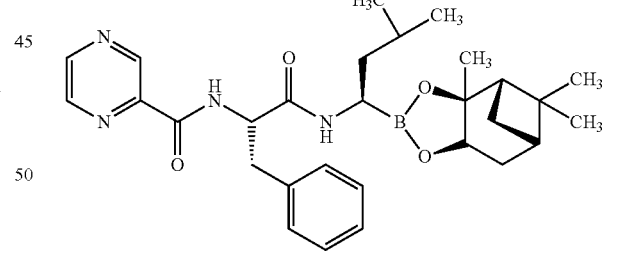

d) deprotecting the compound of formula (VII) to obtain Bortezomib or its anhydride.

2. The process according to claim 1, wherein the first solvent is selected from the group consisting of dichloromethane, dichloroethane, toluene, dimethyl formamide, dimethyl sulfoxide and mixtures thereof.

3. The process according to claim 2, wherein the first solvent is dichloromethane.

4. The process according to claim 1, wherein the first coupling agent is selected from the group consisting of O-(benzotriazol-1-yl)-N,N,N',N'-tetramethyl-uronium tetrafluoroborate (TBTU), dicyclohexylcarbodiimide (DCC), O-benzotriazole-N,N',N'-tetramethyl uronium hexafluoro phosphate (HBTU), benzotriazol-1-yloxytripyrrolidino-phosphonium hexafluorophosphate and 1-ethyl-3-(3-dimethyl-aminopropyl)carbodiimide hydrochloride (EDC HCl).

5. The process according claim 1, wherein the first coupling agent is used with a first additive.

6. The process according to claim 5, wherein the first additive is selected from the group consisting of 1-hydroxy-henzotriazole (HOBT), N-hydroxysuccinimide (HOSu), 2-hydroxypyridine-N-oxide (HOPO), 1-hydroxy-7-azabenzotriazole (HOAt) and N-hydroxy-5-norbornene-2,3-dicarboximide (HONB).

7. The process according to claim 1, wherein the first coupling agent is EDC HCl and the first additive is HOBt.

8. The process according to claim 1, wherein the first base is selected from N,N-diisopropyl ethyl amine and triethyl amine.

9. The process according to claim 1, wherein the inorganic acid is selected from the group consisting of hydrochloric acid, hydrobromic acid and sulphuric acid.

10. The process according to claim 1, wherein the alcohol is selected from the group consisting of ethanol, methanol, isopropanol and mixtures thereof.

11. The process according to claim 1, wherein the alcoholic solution of an inorganic acid is isopropanolic hydrochloric acid.

12. The process according to claim 1, wherein the deprotection of compound (IV) is carried out in situ without isolation of compound (IV).

13. The process according to claim 1, wherein the deprotection of compound (IV) is carried out at a temperature of from 15 to 35° C.

14. The process according to claim 13, wherein the deprotection of compound (IV) is carried out at a temperature of from 20 to 30° C.

15. The process according to claim 1, wherein the second solvent, is selected from the group consisting of toluene and ethyl acetate.

16. The process according to claim 15, wherein the second solvent is toluene.

17. The process according to claim 1, wherein the second coupling agent is selected from the group consisting of O-(benzotriazol-1-yl)-N,N,N',N'-tetramethyluronium tetrafluoroborate (TBTU), dicyclohexylcarbodiimide (DCC), O-benzotriazole-N,N',N'-tetramethyl uronium hexafluoro phosphate (HBTU), benzotriazol-1-yloxytripyrrolidino-phosphonium hexafluorophosphate and 1-ethyl-3-(3-dimethyl-aminopropyl) carbodiimide hydrochloride (EDC HCl).

18. The process according to claim 17, wherein the second coupling agent is TBTU.

19. The process according to claim 1, wherein the second coupling agent is used with a second additive.

20. The process according to claim 19, wherein the second additive is selected from the group consisting of 1-hydroxybenzotriazole (HOBT), N-hydroxysuccinimide (HOSu), 2-hydroxypyridine-N-oxide (HOPO), 1-hydroxy-7-azabenzotriazole (HOAt) and N-hydroxy-5-norbornene-2,3-dicarboximide (HONB).

21. The process according to claim 1, wherein the second base is selected from N,N-diisopropyl ethyl amine and triethyl amine.

22. The process according to claim 1, wherein the deprotection of compound (VII) is carried out by treating compound (VII) with a boronic acid acceptor in an alcoholic solvent.

23. The process according to claim 22, wherein the boronic acid acceptor is selected from the group consisting of isobutyl boronic acid, 2-methyl-1-propyl boronic acid, trifluoroacetic acid, hydrochloric acid, hydrobromic acid and mixtures thereof.

24. The process according to claim 22, wherein the alcoholic solvent is selected from the group consisting of ethanol, methanol, isopropanol, n-propanol, n-butanol, isobutanol and mixtures thereof.

\* \* \* \* \*